(12) United States Patent
Klotz et al.

(10) Patent No.: US 6,969,407 B2
(45) Date of Patent: Nov. 29, 2005

(54) MODULAR RADIAL COMPONENT FOR A TOTAL WRIST ARTHROPLASTY

(75) Inventors: Conrad Klotz, Nappanee, IN (US); Daren Deffenbaugh, Winona Lake, IN (US)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 10/743,202

(22) Filed: Dec. 22, 2003

(65) Prior Publication Data

US 2005/0137709 A1    Jun. 23, 2005

(51) Int. Cl.⁷ .................................................. A61F 2/42
(52) U.S. Cl. .................................................. 623/21.12
(58) Field of Search ......................... 623/21.11–21.13, 623/11.11

(56) References Cited

U.S. PATENT DOCUMENTS

| | | | |
|---|---|---|---|
| 4,085,466 A * | 4/1978 | Goodfellow et al. | 623/20.3 |
| 4,229,840 A * | 10/1980 | Gristina | 623/21.13 |
| 4,259,752 A | 4/1981 | Taleisnik | |
| 4,307,473 A | 12/1981 | Weber | |
| 4,645,505 A | 2/1987 | Swanson | |
| 4,714,476 A | 12/1987 | Ranawat et al. | |
| 5,314,485 A * | 5/1994 | Judet | 623/21.13 |
| 5,458,646 A * | 10/1995 | Giachino et al. | 623/21.12 |
| 5,507,821 A * | 4/1996 | Sennwald et al. | 623/21.13 |
| 5,702,470 A | 12/1997 | Menon | |
| 5,766,258 A * | 6/1998 | Simmen | 623/21.12 |
| 6,059,832 A | 5/2000 | Menon | |
| 6,183,519 B1 * | 2/2001 | Bonnin et al. | 623/21.18 |
| 6,485,520 B1 * | 11/2002 | Hubach et al. | 623/21.13 |
| 2004/0064073 A1 * | 4/2004 | Heldreth | 600/595 |
| 2004/0117025 A1 * | 6/2004 | Reindel | 623/18.11 |

FOREIGN PATENT DOCUMENTS

GB    2278281 A  *  5/1993    .................... 2/58

* cited by examiner

*Primary Examiner*—Suzette J-J Gherbi
(74) *Attorney, Agent, or Firm*—Maginot Moore & Beck (57) ABSTRACT

A radial component of a total wrist arthroplasty prosthesis includes a platform having a stem configured to be implanted within the radius bone. The platform carries an insert that provides the radial articulating component for the wrist joint. The platform and insert include mating features that allow for ready engagement or disengagement of the insert to the platform when the platform is implanted to the radius bone.

11 Claims, 8 Drawing Sheets

MODULAR RADIAL COMPONENT FOR A TOTAL WRIST ARTHROPLASTY

BACKGROUND OF THE INVENTION

The present invention relates to wrist prostheses, and especially to prosthesis for a total wrist arthroplasty. More specifically, the invention concerns a modular prosthesis that permits modification in a revision surgery.

In a total wrist arthroplasty, radial and metacarpal components are engaged to the radius and metacarpal bones, respectively. In a common wrist prosthesis, the radial and metacarpal components define an articulating interface that emulates the natural movement of the patient's wrist. In more recent total wrist prostheses, the articulating interface is defined by ellipsoidal joint elements that eliminate problematic axial rotation and limit the articulation along the axes for flexion/extension and radial/ulnar deflection.

As wrist prostheses have evolved, the trend has been toward modularity. This modularity allows a wrist prosthesis to be specifically tailored to a patient's anatomy. Consequently, some prosthesis offer differently sized radial and metacarpal components. For instance, in some implants, as represented by U.S. Pat. No. 6,485,520, different articulating elements can be selected, with the selected elements being fastened together with machine screws. Thus, in these prior implants, the benefit of modularity is appreciated only when the prosthesis is initially constructed. These implants cannot be modified in a revision surgery without completely removing the affected arthroplasty component.

Until the last decade, total wrist arthroplasty (TWA) was a rarely used option over wrist fusion because of the difficulty in obtaining long-term fixation of the metacarpal/distal side. Improvements in the design of the metacarpal component have led to increasing favor for TWA. In the typical TWA prosthesis, the modularity is restricted to the metacarpal component. One problem with this approach is that the profile height of the metacarpal component must be prominent in order to accept the modular components. This increased height increases the lever arm force exerted on the prosthetic joint. This increased force manifests itself in undesirable loosening of the metacarpal fixation, which can require an invasive revision surgery to remove or repair the loosened metacarpal component.

There is a need in the field of total wrist arthroplasty for a modular system that does not suffer from the difficulties commonly associated with current TWA. There is a further need for a modular system in which the benefits of modularity can be capitalized on in a minimally invasive revision surgery or procedure to restore proper joint tension and spacing of the joint components.

SUMMARY OF THE INVENTION

These needs are met in the present invention by a total wrist arthroplasty prosthesis that places the replaceable modular elements on the radial side of the wrist joint. In one embodiment of the invention, the radial component includes a platform having a stem configured to be implanted within the radius bone. The platform carries an insert that provides the radial or proximal articulating component for the wrist joint. In one feature of the invention, the platform and insert include mating features that allow for ready attachment of the insert to the platform. In a further aspect, the ready attachment also accommodates ready removal of the insert when necessary to replace the insert in a revision procedure, for instance.

In one embodiment a radial component for a wrist prosthesis comprises a stem configured for engagement within the radius bone and a platform attached to the stem. The prosthesis includes an insert defining an articulating surface for mating with an articulating element of a metacarpal wrist component. In one feature of the invention, a mating feature is provided between the insert and the platform to permit engagement of the insert to the platform and removal therefrom without removing the platform from the stem and without removing the stem from the radius.

In certain embodiments, the mating feature includes mating snap-fit elements defined in the platform and the insert. These snap-fit elements can include a female snap-fit element defined in the platform and a male snap-fit element defined in the insert. The platform can define a recess with an opening sized to receive the insert therein and an undercut defined around at least a portion of the opening. With this embodiment, the insert at least one flexible tab configured to engage the undercut within the opening.

In other embodiments, the insert includes two flexible tabs at opposite ends of the insert that can be depressed to activate the mating features. Each of the flexible tabs can include a wedge surface configured to deflect each of the two flexible tabs as the wedge surface contacts the platform when the platform is introduced into the recess. To facilitate insertion and removal, the insert includes means for engagement by an insertion tool, which can be a pair of recesses defined on opposite ends of the insert.

In a further embodiment, the insert defines an inner flange around at least a portion of the insert, and the platform defines a recess with an opening sized to receive the insert therein. The platform further includes at least one flexible tab configured to engage the inner flange when the insert is within the recess.

In other embodiments of the invention, the mating feature includes a first slot extending through the insert, and a second slot extending through the platform, the first and second slots opening toward each other when the insert is engaged to the platform. An opening defined in the platform in communication with the second slot and aligned with the first slot when the insert is engaged to the platform is configured to receive a pin configured to alternatively extend through the second slot and through the opening and the first slot. The first slot and the second slot are preferably angled relative to each other.

In yet another embodiment, the mating feature includes an opening defined in the platform, a recess defined in the insert and arranged to align with the opening when the insert is engaged to the platform, and a locking member pivotably disposed in the opening and configured engage the recess when the locking member is in a locking position and to disengage the recess when the locking member is not in the locking position. In this embodiment, the locking member is eccentrically mounted within the opening and includes a cam surface configured for engaging the recess.

The invention further contemplates a method for implanting a radial component of a wrist prosthesis. This method comprises the steps of implanting a platform in the radius bone, and engaging an insert to the platform when the platform is implanted in the radius bone, the insert defining a bearing surface for mating with an articulating element of a metacarpal wrist component. In another method of the invention, an insert is removed from the platform while the platform is engaged in the bone, and another insert is engaged to the platform.

It is one object to provide a wrist implant that provides the removable modular feature on the radial, rather than the metacarpal, component. It is another object to provide a joint implant that incorporates mating features that permit ready removal and engagement of a bearing insert with a component supported on the bone.

These and other objects and benefits of the invention will be appreciated from the following written description, taken together with the accompanying figures.

DESCRIPTION OF THE PREFERRED EMBODIMENTS

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 1:
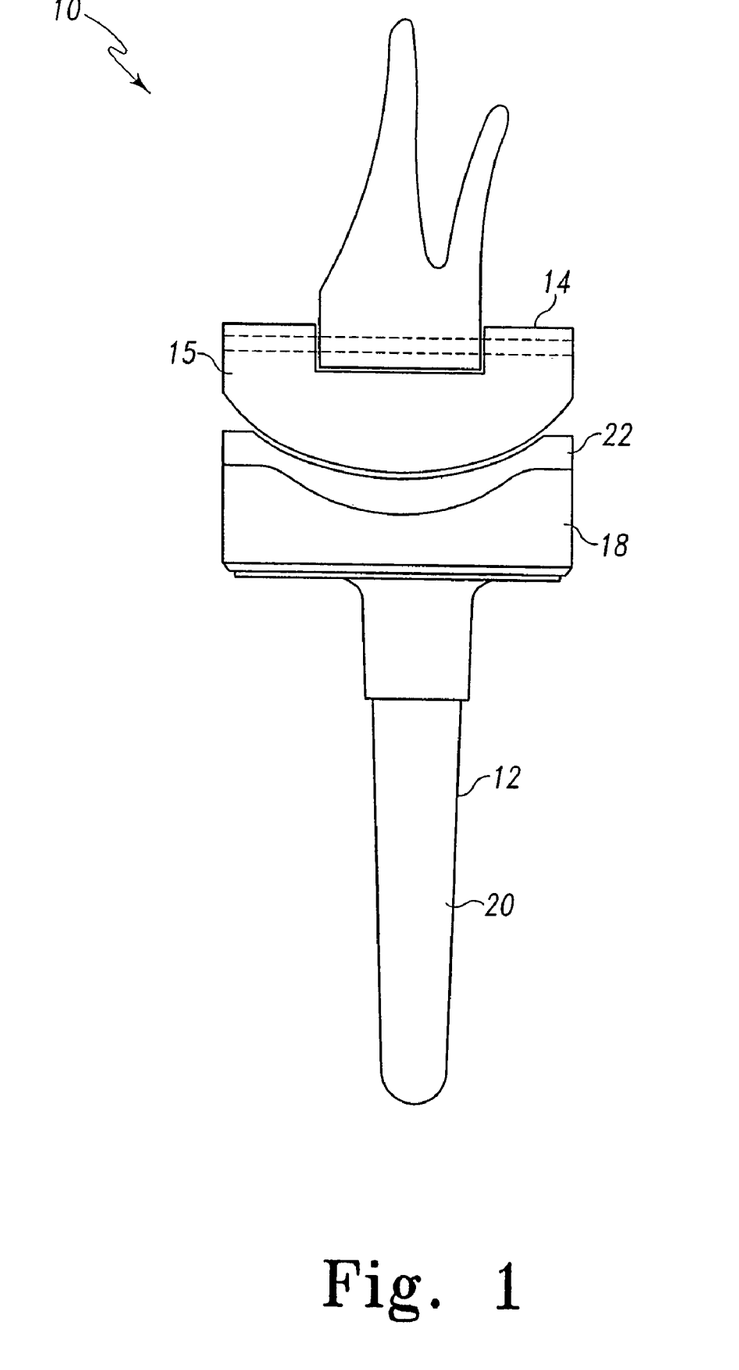
FIG. 1 is a side view of a total wrist arthroplasty (TWA) in accordance with one embodiment of the invention.

A total wrist arthroplasty (TWA) 10, shown in FIG. 1, includes a radial component 12 and a metacarpal component 14. The metacarpal component 14 can be configured in a known manner to engage certain metacarpal bones of the hand. The component includes an articulating element 15 that can follow known configurations. In particular, the element 15 can preferably be in the form of an elliptical male component of the TWA joint.

The radial component 12 can include a platform 18 with a stem 20 projecting therefrom. The platform and stem are configured for implantation in the radius bone in a known manner. The radial component 12 further includes an articulating insert 22 that provides the joint interface with the articulating element 15 of the metacarpal component 14.

Figure 2:
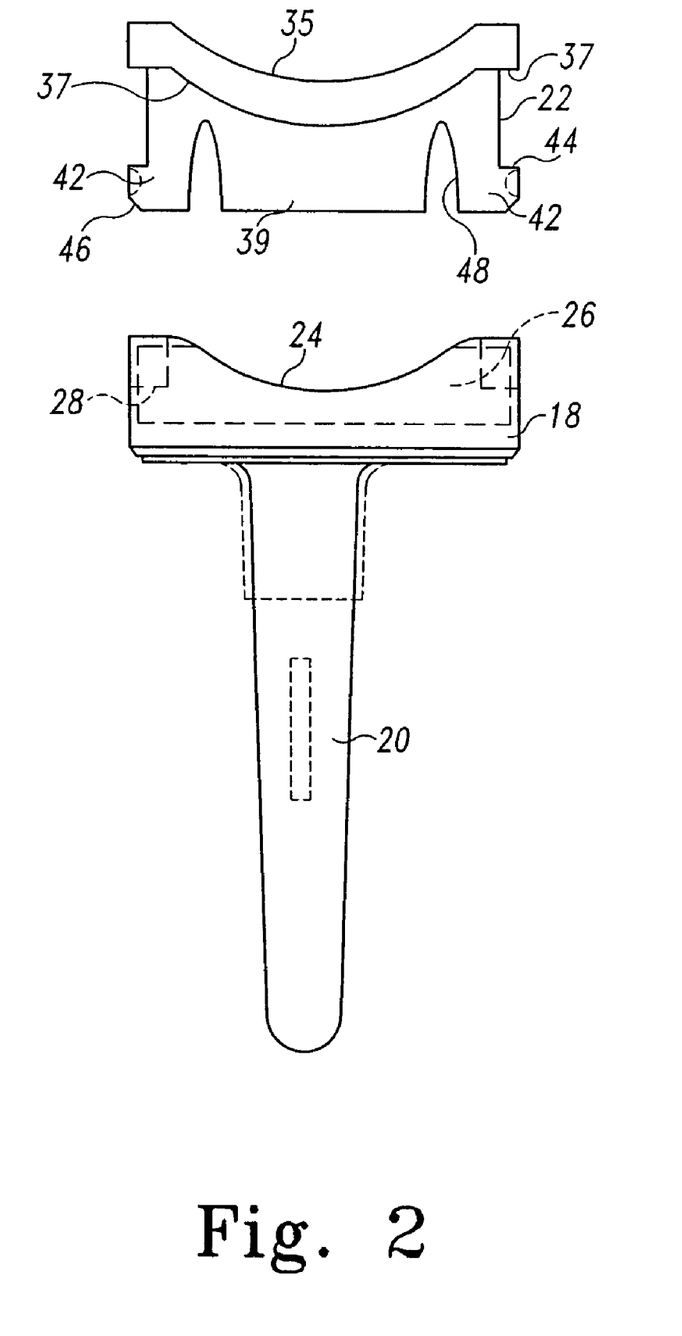
FIG. 2 is an exploded side view of the radial component of the TWA shown in FIG. 1.
Figure 3:
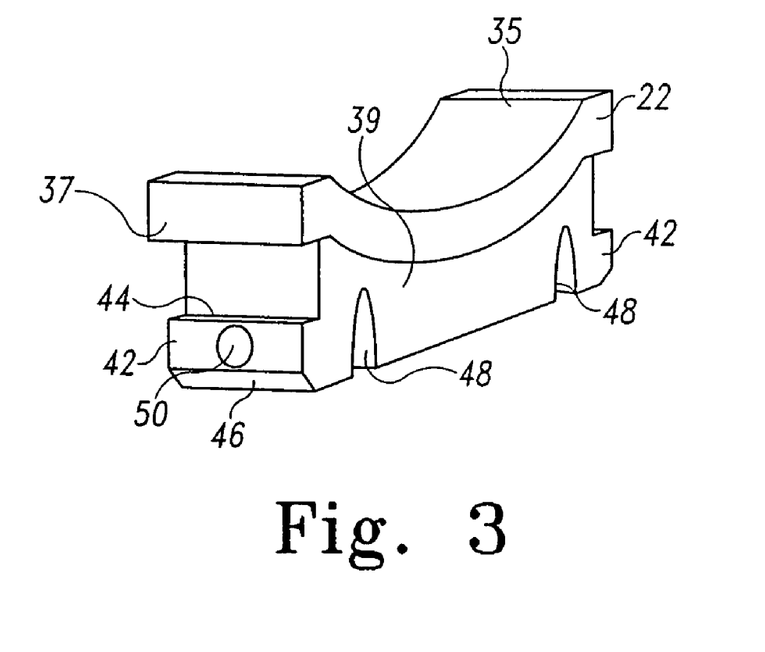
FIG. 3 is an enlarged perspective view of the insert forming part of the radial component shown in FIG. 2.
Figure 4:
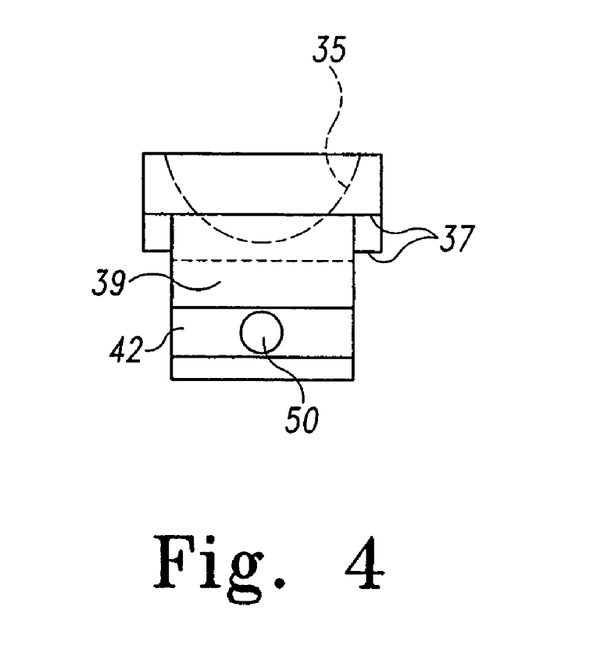
FIG. 4 is an end view of the insert depicted in FIG. 3.

As shown best in FIGS. 2–4, the insert 22 defines a bearing surface 35 that is shaped for sliding and pivoting contact with the articulating element 15 of the metacarpal component 14. As is common for TWAs, the insert 22 can be formed of a polymeric material, such as polyethylene, that serves well in providing a smooth bearing surface 35. Other materials are contemplated, provided they exhibit the same characteristics for sliding/rotating contact with the metacarpal articulating element. For instance, the insert 22 can be formed of a ceramic or a metal.

In order to accept the insert 22, the platform 18 defines a recess 26 with a support edge 24 at the recess opening. The insert 22 includes a body 39 sized to be snugly received within the recess 26 and a flange 37 that rests upon the support edge 24. In accordance with one feature of the present invention, mating features are provided between the platform 18 and insert 22 that bring modularity to the TWA 10. Moreover, these mating features allow the insert 22 to be removed from the platform 18, even when the platform and stem 20 are engaged in a radial bone. This feature can be very beneficial during the initial wrist arthroplasty procedure. In particular, while the optimum dimensions for the TWA components can be divined prior to surgery, it is occasionally necessary to change prosthesis dimensions. For instance, several different sizes of articulating inserts 22 can be provided. In particular, the prominence of the insert can be modified, particularly the thickness of the flange 37 relative to the platform support edge 24. The different inserts can have different flange thicknesses to accommodate different joint anatomies. During a procedure, it may be discovered that the selected TWA components are too tight or too loose relative to the surrounding soft and connective tissues. The surgeon can remove the insert and replace it with a more appropriately sized insert to achieve an optimum TWA.

In accordance with one embodiment of the invention, the mating features can constitute a snap-fit arrangement in which one element snaps into another element. In this embodiment, the mating features include an undercut 28 defined in the insert recess 26 in the platform 18. The articulating insert 22 includes at least two flexible tabs 42 attached to the insert body 39 so that the tabs can be deflected. The flexible tabs 42 define an engagement flange 44 that engages the undercut 28 when the insert body 39 is disposed within the recess 26. Each tab 42 can include a wedge surface 46 opposite the engagement flange 44. This wedge surface contacts the support edge 24 of the platform to deflect the tab inward as the insert is advanced into the recess. Once the engagement flange reaches the undercut 28, the tab snaps outward to lock the insert within the platform.

The tabs 42 are configured to be resiliently deflected inwardly as the insert is pushed into the platform recess. This flexibility can be produced by the inclusion of slots 48 within the insert body 39. Thus, as the tabs deflect, the slots are pinched, and when the engagement flanges 44 reach the undercuts 28, the slots resiliently expand.

Figure 5:
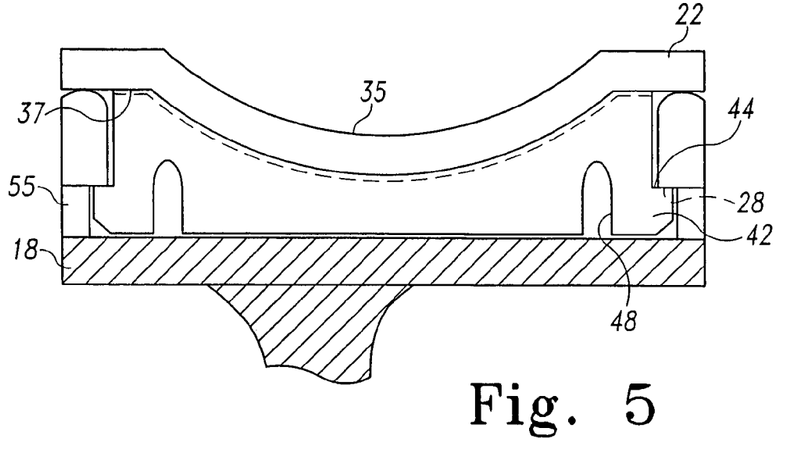
FIG. 5 is an enlarged side partial cross-sectional view of the radial component shown in FIG. 2, with the insert attached to the platform of the component.
Figure 6:
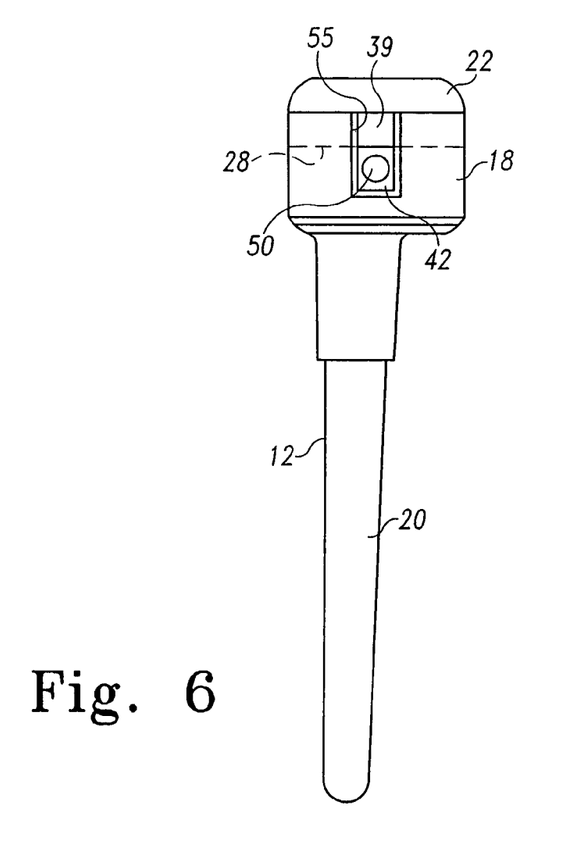
FIG. 6 is an end view of the radial component illustrated in FIG. 2.

As shown in FIG. 3, the flexible tabs 42 are defined at opposite ends of the insert 22. It can be appreciated that the insert can be readily mounted or engaged to the platform 18 by simply pushing the insert into the recess 26. The wedge surfaces 46 of the tabs 42 facilitate initial insertion of the articulating insert into the platform. Once the insert 22 is lodged within the platform 18, as shown in FIG. 5, the insert cannot be dislodged under normal loading of the wrist joint. Removal of the insert requires inward deflection of the flexible tabs 42 until the engagement flanges 44 are clear of the recess undercuts 28. In one embodiment of the invention, the platform is provided with access slots 55 that extend through a portion of the recess undercuts 28, as shown in FIG. 6. This slot exposes the flexible tabs 42 at the opposite sides of the platform. The tabs can be provided with tool engagement dimples 50 that are available through the access slots 55.

Figure 7:
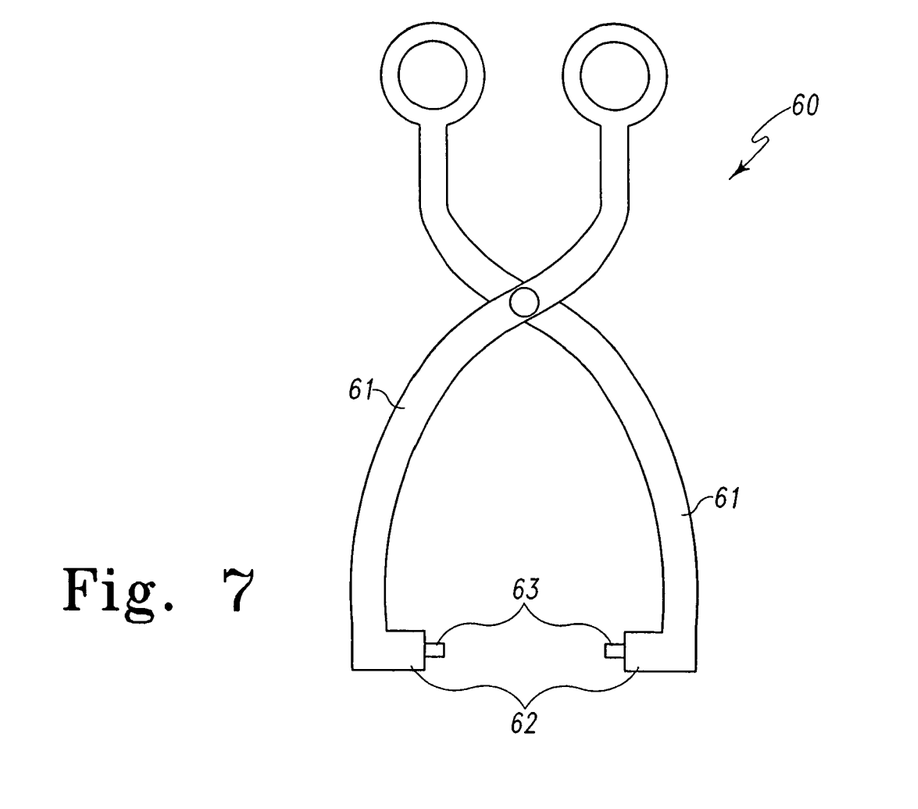
FIG. 7 is a top view of a tool for use in attaching or removing the insert to or from the platform.

A tool 60 can be provided, as shown in FIG. 7, for grasping the insert 22. The tool can be a scissors-type tool with hinged arms 61. The arms can be provided with hubs 62 that are sized to fit within a corresponding access slot 55 and contact the resilient tab within the platform. Preferably, the hubs 62 are provided with engagement posts 63 that are sized to be received within the engagement dimples 50 in the resilient tabs 42. The engagement between the posts and dimples hold the tool 60 in engagement with the insert. The tool can be manipulated to squeeze the flexible tabs 42 together within the platform, thereby releasing the insert from the platform. Once dislodged, the insert can be removed by the tool and a new insert can be loaded onto the platform using the same tool 60.

In the illustrated embodiment, the insert 22 is provided with flexible tabs 42 on both sides of the insert. In this respect, the insert is universal, meaning that it can be mounted within the platform of the radial component 12 in either orientation. Alternatively, the mating feature between the platform and the insert can include comparable flexible tabs on the intermediate sides of the radial component 12. Since these alternative mating features would be disposed on the long side of the implant, providing flexible tabs of a width less than the length of the insert may be preferable.

In yet another alternative, the insert includes only one flexible tab, provided the tab can be deflected enough to allow the insert to be pushed into and removed from the platform. In this alternative, one of the flex slots 48 can be eliminated so that the corresponding tab cannot deflect inward. In one variation on this theme, the engagement flange for the non-deflecting side of the insert can be eliminated. Instead, the non-deflecting side of the insert and the corresponding side of the platform can form a tab and slot or a tongue and groove configuration for sliding engagement between the two elements.

Figure 8:
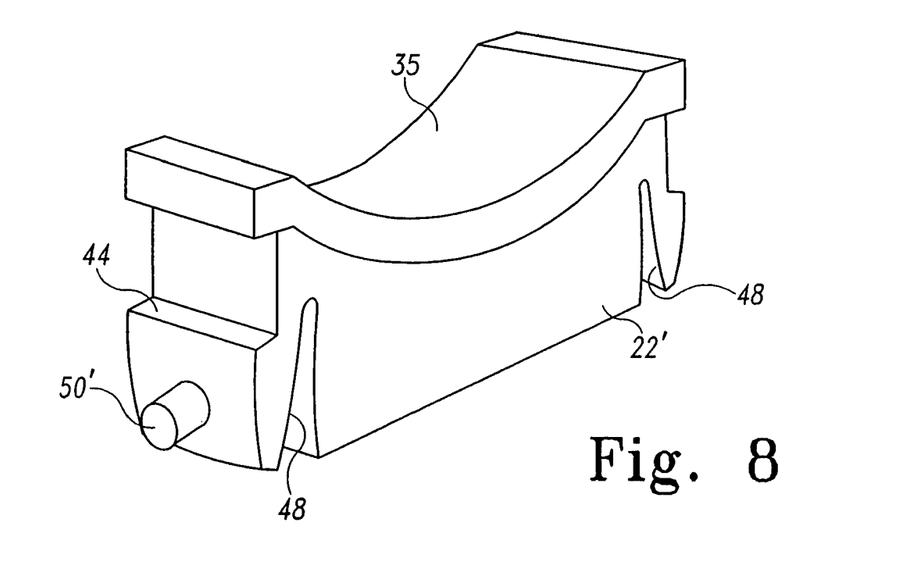
FIG. 8 is a side partial cross-sectional view of a radial component in accordance with a further embodiment of the invention.
Figure 9:
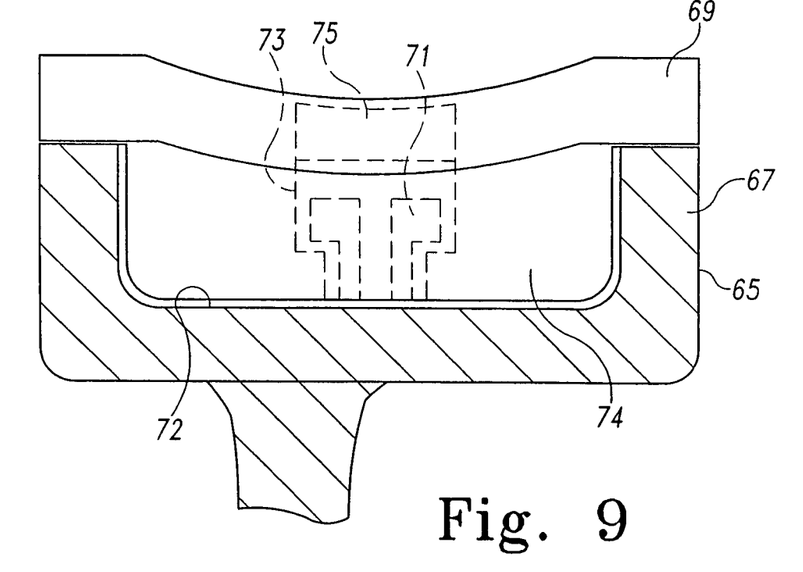
FIG. 9 is a perspective view of an insert for the radial component according to a further embodiment of the invention.

As an alternative, an insert 22' can be provided, as shown in FIG. 8, in which the dimples 50 of the embodiment shown in FIG. 3 are replaced by tabs or posts 50'. These posts 50' can be contacted and depressed against the slots 48 in a manner similar to the dimples described above. The posts 50' preferably project beyond the slot 55 in the radial component 18 so that the posts are accessible outside the implant. With this feature, the posts can be manually depressed and the insert 22' removed by hand, rather than with a tool.

One aspect of the embodiments shown in FIGS. 2–6 is the use of a resilient element that can be deflected for engagement and disengagement of the articulating insert 22 to and from the platform 18 of the radial component 12. The invention contemplates other forms of releasable resilient engagement of the two elements. For instance, as shown in FIG. 8, a radial component 65 can include a platform 67 and an insert 69 that can be configured similar to the like components described above. However, in this embodiment, the mating features can include a collet or snap rivet 71 defined in the recess 72 of the platform. The insert defines a corresponding bore 73 in its body 74 that permits resilient engagement of the snap rivet. A plug 75 can be provided to close the bore when the TWA is fully implanted. The bore 73 is open at the surface of the insert to permit introduction of a tool for compressing the prongs of the collet or snap rivet 71 to permit removal of the insert.

Figure 10:
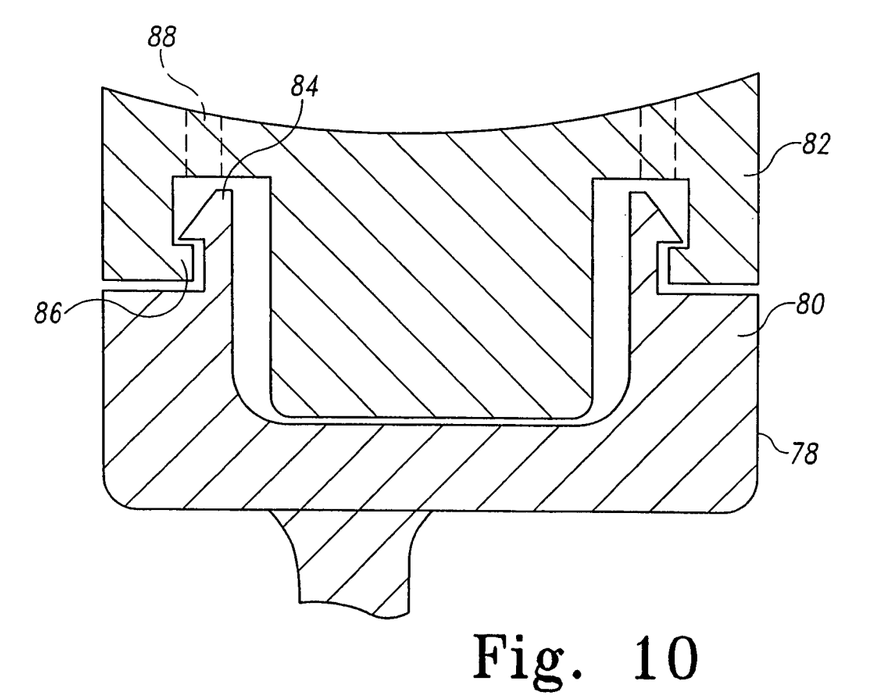
FIG. 10 is a partial side cross-sectional view of an alternative embodiment of a radial component according to the present invention.

In yet another alternative, the resiliently deflectable feature can be situated on the platform. Thus, as shown in FIG. 10, a radial component 78 can include a platform 80 and associated articulating insert 82. The platform can include upwardly projecting flexible tabs 84 that engage an inner flange 86 defined in the insert. An access slot 88 can be defined in the insert 82 to allow introduction of a tool to depress the flexible tabs and release them from the inner flange of the insert.

With the embodiment shown in FIG. 10, the flexible tabs 84 can be integrated into a rim extending around the entire perimeter of the platform. Likewise, the inner flange 86 of the insert 82 can extend around the entire perimeter of the insert. This mating feature as modified can form a snap-fit engagement akin to the reclosable feature on Tupperware®-type food containers. A tool access opening (not shown) can be provided in either the insert or the platform to permit use of a tool to pry loose a portion of the mating engagement.

Figure 11:
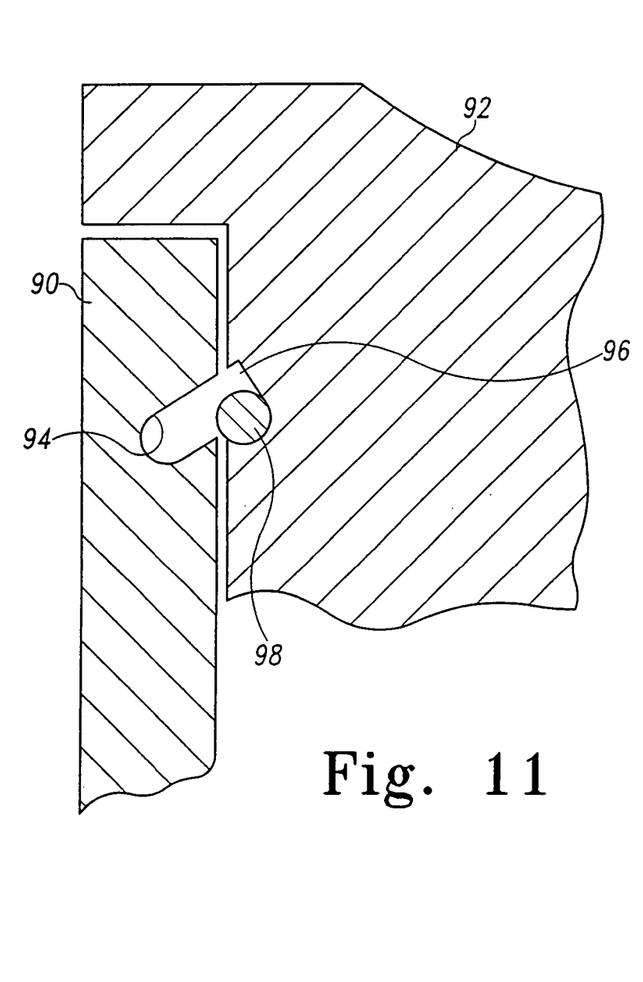
FIG. 11 is a partial enlarged cross-sectional view of a radial component in accordance with an embodiment of the invention that utilizes a separate element to engage the elements of the radial component.
Figure 12:
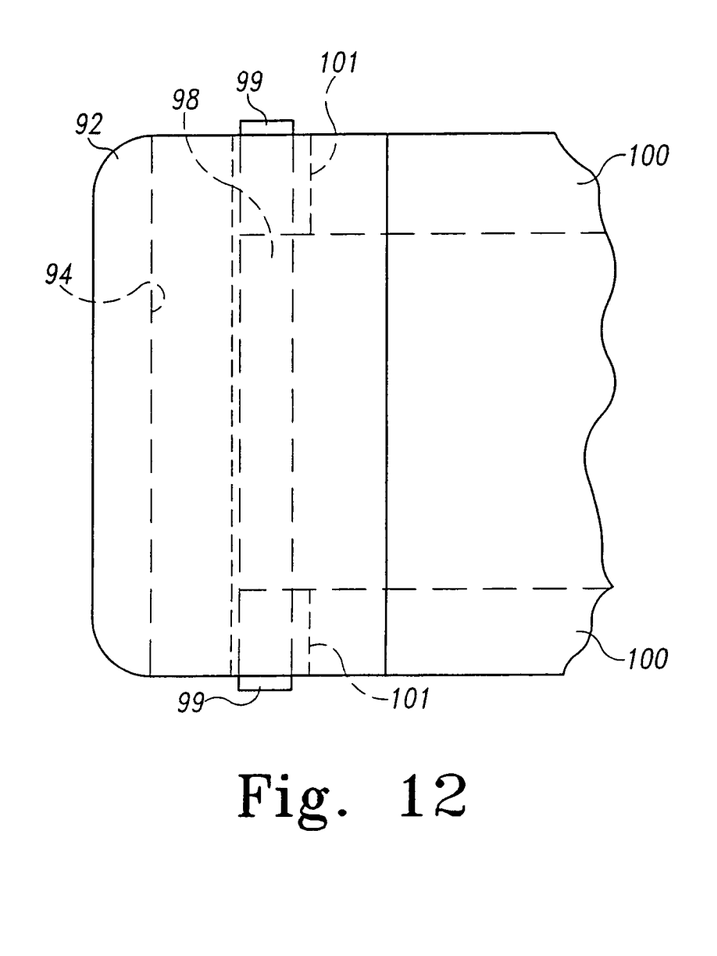
FIG. 12 is a top view of the radial component shown in FIG. 11.

In the aforementioned embodiments of the invention, a resilient deformable mating feature is provided to permit engagement and disengagement between the insert and the platform. In additional embodiments of the invention, the mating feature includes an element separate from the platform and insert. One example is depicted in FIGS. 11–12. In this embodiment, a platform 90 receives an articulating insert 92. The platform defines an angled slot 94 that extends across the width of the platform, as shown in FIG. 12. The insert 92 also defines an angled slot 96 that angles away from the slot 94. A pin 98 is configured to fit snugly within at least the slot 96 in the insert and to be able to pass freely between the two slots 94, 96. The platform defines openings 101 through its side walls 100 so that the pin 98 can pass through both the insert 92 and the platform side walls 100, as shown in FIG. 12. When the pin is in the position shown in FIG. 11, the insert is locked to the platform.

The ends 99 of the pin 98 are accessible outside the platform so that the pin can be manipulated from the slot 96 in the insert to the slot 94 in the platform. When the pin is moved into the angled slot 94, it is clear of the insert so that the insert can be removed from the platform. The angled slot 96 in the articulating insert 92 can be arranged to efficiently capture the pin 96 within the insert. In addition, the slot can be configured to resiliently grip the pin. The opening 101 in the side walls 100 of the platform can emulate the configuration of the angled slot 96. It is of course understood that the opening 101 must communicate with the angled slot 94 in the platform.

Figure 13:
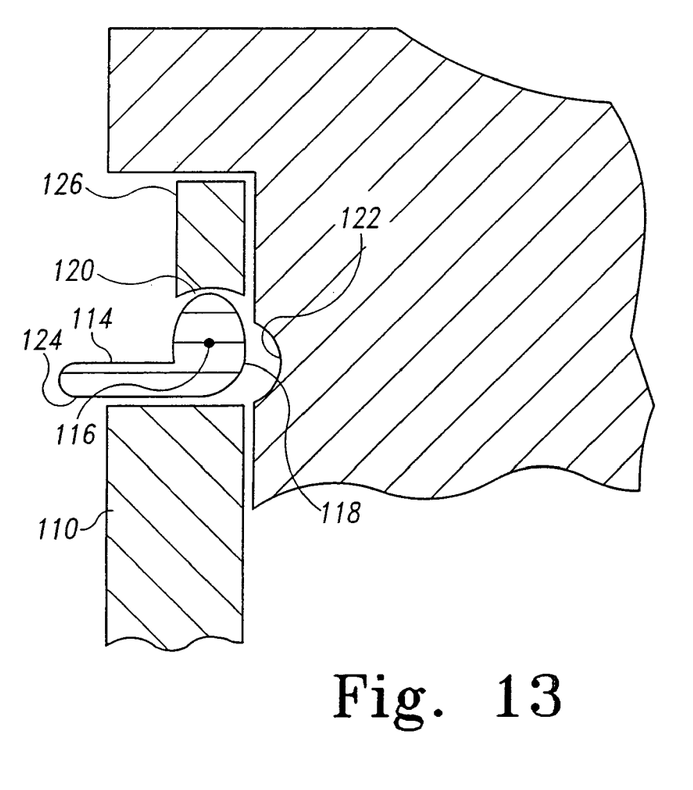
FIG. 13 is a partial enlarged cross-sectional view of the radial component according to another embodiment of the invention, with a separate locking element shown in its unlocked position.
Figure 14:
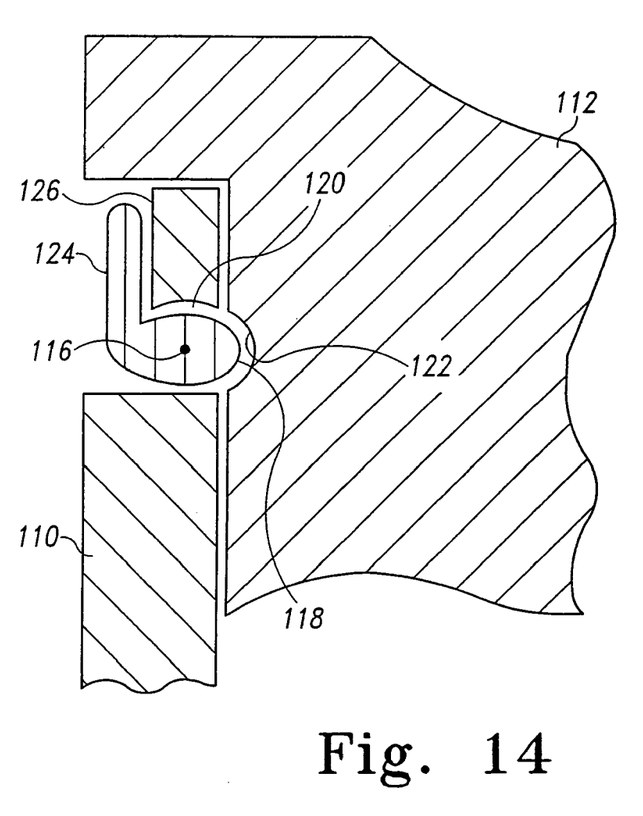
FIG. 14 is partial enlarged cross-sectional view of the radial component shown in FIG. 13, with the separate locking element shown in its locked position.

Following a similar approach is the embodiment shown in FIGS. 13–14. In this embodiment, a platform 110 receives an insert 112. The platform includes a cam lock 114 that is pivotably mounted at a pivot point 116 within an opening 120 in the platform. This opening 120 coincides with a dimple or recess 122 defined in the insert 112, wherein the recess is aligned with the opening when the insert is mounted within the platform.

The cam lock 114 includes a cam surface 118 that is configured so that the cam surface is wholly disposed within the opening 120, as shown in FIG. 13, to allow placement of the insert into the platform. The cam lock 114 includes an arm 124 that can be used to rotate the lock about its pivot point 116 so that the cam surface 118 now extends through the opening 120 and into the recess 122. In this position, the cam lock arm 124 can be disposed within an indentation 126 in the platform so that the cam lock is essentially flush with the platform outer surface. In order to accomplish this motion, the cam lock is preferably eccentrically mounted and the cam surface oblong in shape.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A radial component for a wrist prosthesis comprising:
   a stem configured for engagement within the radius bone;
   a platform attached to said stem;
   an insert defining an articulating surface for mating with an articulating element of a metacarpal wrist component; and
   a mating feature between said insert and said platform to permit engagement of said insert to said platform and removal therefrom without removing said platform from said stem and without removing said stem from the radius,
   wherein said mating feature includes mating snap-fit elements defined in said platform and said insert,
   wherein said mating snap-fit elements includes a female snap-fit element defined in said platform and a male snap-fit element defined in said insert,
   wherein said platform defines a recess with an opening sized to receive said insert therein and an undercut defined around at least a portion of said opening; and
   wherein said insert includes at least one flexible tab configured to engage said undercut within said opening.

2. The radial component according to claim 1, wherein said insert includes two flexible tabs at opposite ends of said insert.

3. The radial component according to claim 1, wherein each of said flexible tabs includes a wedge surface configured to deflect each of said two flexible tabs as the wedge surface contacts said platform when said platform is introduced into said recess.

4. The radial component according to claim 1, wherein said insert includes a body, said body defining a slot adjacent said at least one flexible tab.

5. A radial component for a wrist prosthesis comprising:
   a stem configured for engagement within the radius bone;
   a platform attached to said stem;
   an insert defining an articulating surface for mating with an articulating element of a metacarpal wrist component; and
   a mating feature between said insert and said platform to permit engagement of said insert to said platform and removal therefrom without removing said platform from said stem and without removing said stem from the radius,
   wherein said mating feature includes:
      a first slot extending through said insert;
      a second slot extending through said platform, said first and second slots opening toward each other when said insert is engaged to said platform;
      an opening defined in said platform in communication with said second slot and aligned with said first slot when said insert is engaged to said platform; and
      a pin configured to alternatively extend through said second slot and through said opening and said first slot.

6. The radial component according to claim 5, wherein said first slot and said second slot are angled relative to each other.

7. A radial component for a wrist prosthesis comprising:
   a stem configured for engagement within the radius bone;
   a platform attached to said stem;
   an insert defining an articulating surface for mating with an articulating element of a metacarpal wrist component; and
   a mating feature between said insert and said platform to permit engagement of said insert to said platform and removal therefrom without removing said platform from said stem and without removing said stem from the radius,
   wherein said mating feature includes:
      an opening defined in said platform;
      a recess defined in said insert and arranged to align with said opening when said insert is engaged to said platform; and
      a locking member pivotably disposed in said opening and configured engage said recess when said locking member is in a locking position and to disengage said recess when said locking member is not in said locking position,
   wherein said locking member is eccentrically mounted within said opening and includes a cam surface configured for engaging said recess.

8. The radial component according to claim 7, wherein said locking member includes an arm extending from said cam surface, said arm manipulated to pivot said locking member.

9. The radial component according to claim 8, wherein said platform defines an indentation for receiving said arm when said locking member is in said locking position.

10. A method for implanting a radial component of a wrist prosthesis, comprising:
    implanting a platform in the radius bone;
    engaging an insert to the platform when the platform is implanted in the radius bone, the insert defining a bearing surface for mating with an articulating element of a metacarpal wrist component;
    while the platform is implanted in the radius bone, removing the insert from the platform; and
    engaging another insert to the platform.

11. A method for implanting a radial component of a wrist prosthesis, comprising:
    implanting a platform in the radius bone;
    engaging an insert to the platform, the insert defining a bearing surface for mating with an articulating element of a metacarpal wrist component;
    while the platform is implanted in the radius bone, removing the insert from the platform; and
    engaging another insert to the platform.

* * * * *